(12) United States Patent
Chatterjee et al.

(10) Patent No.: US 9,975,853 B2
(45) Date of Patent: May 22, 2018

(54) TETRAHYDROISOQUINOLINONE DERIVATIVES AND THEIR USE IN THE INHIBITION OF THE HSP70 PROTEIN

(71) Applicant: Julius-Maximilians-Universitaet Wuerzburg, Wuerzburg (DE)

(72) Inventors: Manik Chatterjee, Wuerzburg (DE); Andreas Hartung, Rannungen (DE); Ulrike Holzgrabe, Eibelstadt (DE); Elisabeth Mueller, Wuerzburg (DE); Ulrich Peinz, Peine (DE); Christoph Sotriffer, Gerbrunn (DE); David Zilian, Wuerzburg (DE)

( * ) Notice: Subject to any disclaimer, the term of this patent is extended or adjusted under 35 U.S.C. 154(b) by 0 days. days.

(21) Appl. No.: 15/316,279

(22) PCT Filed: Jun. 3, 2014

(86) PCT No.: PCT/EP2014/061495
§ 371 (c)(1),
(2) Date: Dec. 5, 2016

(87) PCT Pub. No.: WO2015/185114
PCT Pub. Date: Dec. 10, 2015

(65) Prior Publication Data
US 2017/0152229 A1    Jun. 1, 2017

(51) Int. Cl.
C07D 217/16 (2006.01)
C07D 217/26 (2006.01)
C07D 401/12 (2006.01)

(52) U.S. Cl.
CPC ......... C07D 217/26 (2013.01); C07D 401/12 (2013.01)

(58) Field of Classification Search
CPC ............................ C07D 217/16; C07D 401/12
See application file for complete search history.

(56) References Cited

U.S. PATENT DOCUMENTS 5,916,899 A * 6/1999 Kiely .................... C07D 217/26
506/15

FOREIGN PATENT DOCUMENTS

WO    WO 2004/004727    1/2004

OTHER PUBLICATIONS

Chemical Abstracts Service, CAS Registry No. 1024289-66-4 (Jun. 1, 2008).
Chemical Abstracts Service, CAS Registry No. 442859-49-6 (Aug. 7, 2002).
Chemical Abstracts Service, CAS Registry No. 442859-45-2 (Aug. 7, 2002).
Chemical Abstracts Service, CAS Registry No. 442859-44-1 (Aug. 7, 2002).
Chemical Abstracts Service, CAS Registry No. 442859-43-0 (Aug. 7, 2002).
Chemical Abstracts Service, CAS Registry No. 442859-35-0 (Aug. 7, 2002).
Chemical Abstracts Service, CAS Registry No. 442859-28-1 (Aug. 7, 2002).
Chemical Abstracts Service, CAS Registry No. 442859-23-6 (Aug. 7, 2002).
Chemical Abstracts Service, CAS Registry No. 442859-19-0 (Aug. 7, 2002).
Chemical Abstracts Service, CAS Registry No. 442859-18-9 (Aug. 7, 2002).
Chemical Abstracts Service, CAS Registry No. 442859-17-8 (Aug. 7, 2002).
Chemical Abstracts Service, CAS Registry No. 442859-04-3 (Aug. 7, 2002).
Chemical Abstracts Service, CAS Registry No. 442858-96-0 (Aug. 7, 2002).
Chemical Abstracts Service, CAS Registry No. 442858-95-9 (Aug. 7, 2002).
Chemical Abstracts Service, CAS Registry No. 442858-94-8 (Aug. 7, 2002).
Chemical Abstracts Service, CAS Registry No. 442858-89-1 (Aug. 7, 2002).
Chemical Abstracts Service, CAS Registry No. 442858-86-8 (Aug. 7, 2002).
Chemical Abstracts Service, CAS Registry No. 442858-84-6 (Aug. 7, 2002).
Chemical Abstracts Service, CAS Registry No. 442858-83-5 (Aug. 7, 2002).
Chemical Abstracts Service, CAS Registry No. 442858-82-4 (Aug. 7, 2002).
Chemical Abstracts Service, CAS Registry No. 442858-81-3 (Aug. 7, 2002).
Chemical Abstracts Service, CAS Registry No. 442858-80-2 (Aug. 7, 2002).
Chemical Abstracts Service, CAS Registry No. 442858-74-4 (Aug. 7, 2002).
Chemical Abstracts Service, CAS Registry No. 442858-73-3 (Aug. 7, 2002).
Chemical Abstracts Service, CAS Registry No. 442858-72-2 (Aug. 7, 2002).
Chemical Abstracts Service, CAS Registry No. 442858-71-1 (Aug. 7, 2002).
Chemical Abstracts Service, CAS Registry No. 442858-70-0 (Aug. 7, 2002).
Chemical Abstracts Service, CAS Registry No. 442858-69-7 (Aug. 7, 2002).
Chemical Abstracts Service, CAS Registry No. 442858-68-6 (Aug. 7, 2002).
Chemical Abstracts Service, CAS Registry No. 442858-54-0 (Aug. 7, 2002).
Chemical Abstracts Service, Cas Registry No. 442858-53-9 (Aug. 7, 2002).

* cited by examiner

Primary Examiner — D Margaret M Seaman

(57) ABSTRACT

The present invention relates to tetrahydroisoquinolinone derivatives, a pharmaceutical composition comprising the same and the use of these derivatives in the inhibition of the Hsp70 protein. The compounds are useful in the treatment or inhibition of cancer, autoimmune disease, rheumatoid arthritis, inflammatory bowel disease and psoriasis.

14 Claims, 3 Drawing Sheets

TETRAHYDROISOQUINOLINONE DERIVATIVES AND THEIR USE IN THE INHIBITION OF THE HSP70 PROTEIN

PRIORITY

This application corresponds to the U.S. national phase of International Application No. PCT/EP2014/061495 filed Jun. 3, 2014, the contents of which are incorporated by reference herein in their entirety.

FIELD OF THE INVENTION

The present invention relates to tetrahydroisoquinolinone derivatives, a pharmaceutical composition comprising the same and the use of these derivatives in the inhibition of the Hsp70 protein. The compounds are useful in the treatment or inhibition of cancer, autoimmune disease, rheumatoid arthritis, inflammatory bowel disease and psoriasis.

BACKGROUND OF THE INVENTION

Multiple myeloma is a hematological B cell malignancy. The vast majority of the affected cells are localized within the bone marrow, where they promote bone destruction and impair normal hematopoiesis. Improved methods in stem cell therapies and novel drugs such as proteasome inhibitors and derivatives of thalidomide have lead to significant improvement in overall survival of myeloma patients, which currently stands at about five years. Nevertheless, multiple myeloma remains incurable and its clinical cause is usually characterized by good initial response to treatment followed after some time by relapse and an eventual development of general resistance to current therapies.

It has been demonstrated that the heat shock protein 70 (Hsp70) plays an essential pathogenic role in multiple myeloma. In recent years, increasing evidence has suggested Hsp70 as a potential anti-cancer target. It has been previously observed that dual targeting of the Hsp70 isoforms Hsp72 and Hsp73 induces tumor-specific apoptosis. However, to date only a limited number of Hsp70 inhibitors is available, while efficient and selective pharmacological agents are almost completely missing.

US 2009/0068144 A1 discloses tetrahydroisoquinolin-1-one derivatives for the treatment of cancer. The exemplified compounds bear a 4-carboxylic acid substituent being present as free acid or for example as —CONH lower alkyl moiety.

US 2005/0124614 A1 discloses 3,4-dihydroisoquinolin-1-ones that are said to be activators of caspases and inducers of apoptosis. Most of the exemplified compounds bear no or only small substituents, like methyl or propyl at position 2 of the tetrahydroisoquinolinone ring. Furthermore, the carboxamide substituent at position 4 may bear relatively small substituents like hydrogen and alkyl.

US 2010/0227866 A1 discloses a broad variety of tetrathydroisoquinolin-1-one derivatives which are said to be useful as therapeutic agents for irritable bowel syndrome.

There is therefore still a need for further compounds exhibiting improved Hsp70 protein inhibiting activity and being useful for the treatment of cancer, in particular of multiple myeloma.

SUMMARY OF THE INVENTION

The present inventors have found that certain tetrahydroisoquinolin-1-one derivatives bearing specific substituents exhibit high Hsp70 protein inhibition activity and therefore are useful in the treatment of cancer, in particular in the treatment of multiple myeloma.

The present invention therefore relates to a compound represented by the following formula (I) or a pharmaceutically acceptable salt thereof

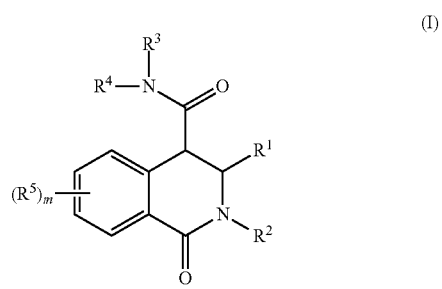

wherein
$R^1$ is phenyl, pyridinyl or pyrimidinyl, each of which may be substituted by one or more substituents Y;
$R^2$ is phenyl, pyridinyl or pyrimidinyl, each of which may be substituted by one or more substituents Y';
$R^3$ is phenyl, pyridinyl or pyrimidinyl, each of which may be substituted by one or more substituents Y";
Y, Y' and Y" are independently selected from halogen, $C_{1-6}$ alkyl, $C_{1-6}$ haloalkyl, hydroxy, $C_{1-6}$ alkoxy, $C_{1-6}$ haloalkoxy, nitro, —$NR^6R^7$, —CO—$R^8$, —CO—$NR^6R^7$, —$COOR^6$, and —CO—$NR^6$—CO—$R^8$;
$R^4$ is hydrogen or $C_{1-4}$ alkyl;
$R^5$ is halogen, hydroxy, $C_{1-6}$ alkyl, $C_{1-6}$ alkoxy, $C_{1-6}$ haloalkyl, $C_{1-6}$ haloalkoxy, nitro or —$NR^6R^7$;
$R^6$ and $R^7$ are independently selected from hydrogen and $C_{1-6}$ alkyl;
$R^8$ is $C_{1-6}$ alkyl;
and
m is an integer of 0 to 3, wherein if m is 2 or 3 the substituents $R^5$ may be selected independently of each other.

These compounds exhibit high cell death-inducing potential in the multiple myeloma cell line INA-6 and at the same time show low toxicity.

Among these compounds 2,3-bis(4-methoxyphenyl)-N-(6-methylpyridin-2-yl)-1-oxo-1,2,3,4-tetrahydroisoquinoline-4-carboxamide and 2,3-bis(4-methoxyphenyl)-N-pyridin-2-yl-1-oxo-1,2,3,4-tetrahydroquinoline-4-carboxamide are reported catalog compounds having CAS registry numbers 442858-86-8 and 442858-72-2, respectively. These compounds are therefore excluded from the scope of the compound claim but since their ability to inhibit the Hsp70 protein and their utility in the treatment of cancer and other diseases has not yet been reported they are included in the scope of the medical use claims.

BRIEF DESCRIPTION OF THE FIGURES

The data presented in FIGS. 1A-1C demonstrates that trans-7b treatment decreases HSP72 and HSP73 but not HSP90 expression, and inhibits HSP70/HSP90 multi-chaperone activity leading to downregulation of constitutive expression levels of well-defined HSP70-dependent client proteins in myeloma cells. In particular.

The data presented in FIGS. 2A to 2C demonstrates that trans-7b treatment leads to activation of the caspases 9 and 3, and induction of apoptosis in malignant INA-6 multiple myeloma (MM) cells but not in non-malignant peripheral blood mononuclear cells (PBMCs). The experimental data presented shows that INA-6 tumor cells are highly sensitive (in a low micromolar range) towards trans-7b treatment, whereas primary PBMCs lack any cytotoxic effect even in higher micromolar concentrations. In particular.

The data in FIG. 3 shows that concomitant inhibition of HSP72/73 by trans-7b strongly enhanced the apoptotic effect of the HSP90 inhibitor NVP-AUY922. In particular.

DETAILED DESCRIPTION OF THE PREFERRED EMBODIMENTS

Figure 1:
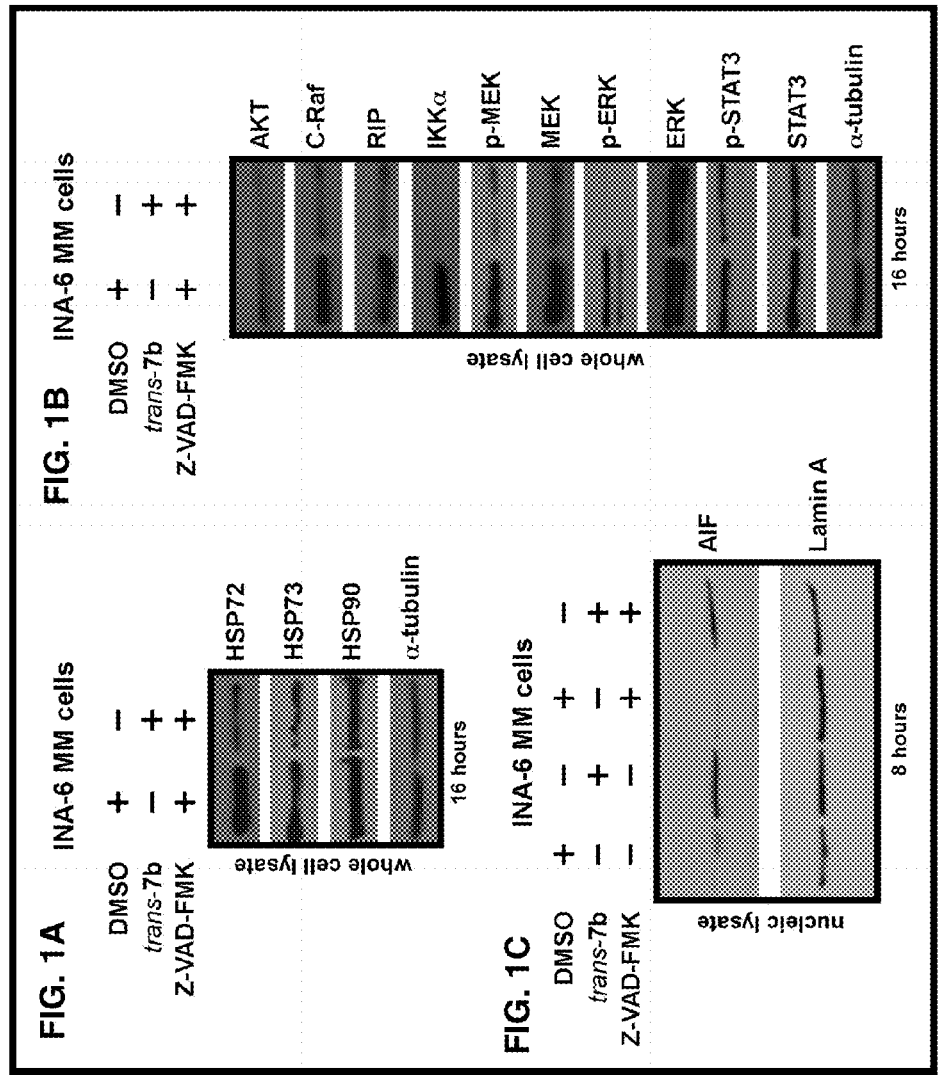
FIG. 1A depicts the expression of HSP72, HSP73, HSP90, and α-tubulin in INA-6 multiple myeloma cells incubated either with DMSO as a solvent control or with the compound trans-7b (0.6 μM), and additionally incubated with the pan-caspase inhibitor Z-VAD-FMK (50 µM) prior to Western blot analysis.
FIG. 1B depicts the expression of several well-defined HSP70/HSP90 chaperon-dependent signaling intermediates or their substrates.
FIG. 1C depicts the HSP70-dependent nuclear translocation of the apoptosis-inducing factor (AIF).

In the context of the present invention the term "halogen" includes fluoro, chloro, bromo and iodo, preferably fluoro and chloro.

The term "$C_{1-6}$ alkyl" includes methyl, ethyl, n-propyl, iso-propyl, n-butyl, iso-butyl, tert-butyl, pentyl and hexyl, preferably methyl, ethyl, n-propyl and iso-propyl, more preferably methyl and ethyl.

The term "$C_{1-6}$ haloalkyl" includes the above described $C_{1-6}$ alkyl groups being substituted with one or more halogen atoms which are defined as above. A suitable haloalkyl is, for example, trifluoromethyl.

The term "$C_{1-6}$ alkoxy" includes alkoxy groups containing the above described $C_{1-6}$ alkyl residues, such as methoxy, ethoxy, n-propoxy and iso-propoxy, in particular methoxy and ethoxy.

The term "$C_{1-6}$ haloalkoxy" includes a haloalkoxy group comprising a $C_{1-6}$ haloalkyl moiety as described above.

The term "$C_{1-4}$ alkyl" defines methyl, ethyl, n-propyl, iso-propyl, n-butyl, iso-butyl and tert-butyl, preferably methyl and ethyl.

The pyridinyl and pyrimidinyl residues represented by $R^1$, $R^2$ and $R^3$ may be attached to the remaining molecule by any of their carbon atoms. Preferably these residues are pyridin-2-yl, pyrimidin-2-yl or pyrimidin-4-yl.

$R^1$ preferably is phenyl. $R^2$ preferably is phenyl. Most preferably, both, $R^1$ and $R^2$ are phenyl.

$R^3$ preferably is phenyl or pyridinyl, in particular pyridin-2-yl or pyridin-3-yl.

$R^1$, $R^2$ and $R^3$ may be substituted by one or more substituents which are independently selected from halogen, $C_{1-6}$ alkyl, $C_{1-6}$ haloalkyl, hydroxyl, $C_{1-6}$ alkoxy and $C_{1-6}$ haloalkoxy, preferably from halogen, $C_{1-6}$ alkyl and $C_{1-6}$ alkoxy. For the substituents Y and Y' in $R^1$ and $R^2$ halogen, methyl, ethyl, methoxy and ethoxy are preferred. For Y" in $R^3$ methyl and ethyl are preferred.

The number of substituents Y, Y' and Y" is not particularly limited, however, for $R^1$ and $R^2$ each one substituent Y and Y', respectively, is preferred and for $R^3$ one or two substituents Y" are preferred.

Y, Y' and Y" may be present at any carbon atom of the phenyl, pyridinyl or pyrimidinyl represented by $R^1$, $R^2$ and $R^3$, respectively. Preferably, $R^1$ and $R^2$, if substituted, bear at least one substituent at ortho or para position to the position at which $R^1$ and $R^2$ are attached to the tetrahydroisoquinolin-1-one ring. Preferably, $R^1$ and $R^2$ do not bear substituents only at one or both of their meta positions. Most preferably, $R^1$ and/or $R^2$ bear one substituent at para position.

In a further preferred embodiment of the present invention, $R^1$ and/or $R^2$ bear one substituent selected from halogen, methoxy and ethoxy at para position to the position at which $R^1$ and $R^2$ are attached to the tetrahydrosioquinolin-1-one ring. In this embodiment both, $R^1$ and $R^2$ preferably are phenyl. More preferably $R^1$ and/or $R^2$ are phenyl or 4-methoxyphenyl. Most preferred $R^1$ is 4-methoxyphenyl and $R^2$ is phenyl.

One or more substituents Y" may be present at any carbon atom of the phenyl, pyridinyl and pyrimidinyl represented by $R^3$. Preferably $R^3$ bears one substituent Y" in meta position to the position at which $R^3$ is attached to the carboxamide moiety or two substituents Y" both at meta position to the position at which $R^3$ is attached to the carboxamide moiety. Thus, preferred substituents $R^3$ are pyridin-2-yl, 6-methylpyridin-2-yl, m-tolyl and 3,5-dimethylphenyl. These preferred substituents $R^3$ are preferably further combined with the above described preferred substituents $R^1$ and $R^2$, in particular with phenyl and 4-methoxyphenyl for $R^1$ and/or $R^2$.

The tetrahydroisoquinolin-1-one moiety in the compound of the present invention may bear up to three further substituents $R^5$. If there are two or three substituents $R^5$, these may be selected independently of each other. Those compounds which do not contain any substituent $R^5$ are preferred.

As the compound of the present invention has two chiral centers, four stereoisomers are possible. Among these the trans-enantiomers show higher binding activity, they are preferred over the cis-enantiomers. A cell-viability assay revealed that the trans-R,R enantiomer was more active than the trans-S,S enantiomer. Therefore, the trans-R,R enantiomer of the compound of the present invention is most preferred.

The following compounds are particularly preferred:
trans-N-(6-Methylpyridin-2-yl)-1-oxo-2,3-diphenyl-1,2,3, 4-tetrahydroisoquinoline-4-carboxamide,
trans-3-(4-Methoxyphenyl)-N-(6-methylpyridin-2-yl)-1-oxo-2-phenyl-1,2,3,4-tetrahydroisoquinoline-4-carboxamide,
trans-2-(4-Methoxyphenyl)-N-(6-methylpyridin-2-yl)-1-oxo-3-phenyl-1,2,3,4-tetrahydroisoquinoline-4-carboxamide,
trans-2,3-Bis(4-methoxyphenyl)-1-oxo-N-(m-tolyl)-1,2,3,4-tetrahydroisoquinoline-4-carboxamide,
trans-N-(3,5-Dimethylphenyl)-2,3-bis(4-methoxyphenyl)-1-oxo-1,2,3,4-tetrahydroisoquinoline-4-carboxamide, trans-2,3-Bis(4-fluorophenyl)-N-(6-methylpyridin-2-yl)-1-oxo-1,2,3,4-tetrahydroisoquinoline-4-carboxamide,
trans-2,3-Bis(4-chlorophenyl)-N-(6-methylpyridin-2-yl)-1-oxo-1,2,3,4-tetrahydroisoquinoline-4-carboxamide,
trans-3-(4-Methoxyphenyl)-1-oxo-2-phenyl-N-(pyrimidin-2-yl)-1,2,3,4-tetrahydroisoquinoline-4-carboxamide,
trans-3-(4-Methoxyphenyl)-1-oxo-2-phenyl-N-(pyridin-3-yl)-1,2,3,4-tetrahydroisoquinoline-4-carboxamide, and
trans-N-(4,6-Dimethylpyridin-2-yl)-3-(4-methoxyphenyl)-1-oxo-2-phenyl-1,2,3,4-tetrahydroisoquinoline-4-carboxamide.

The compounds of the present invention exhibit high inhibition of the Hsp70 protein. Therefore, they are suitable for the preparation of pharmaceutical compositions comprising these compounds. The choice of a pharmaceutical composition depends on various factors such as the mode of drug administration, such as oral, systemic or parenteral administration. The preferred manner of administration is oral or parenteral using a convenient daily dosage regimen, which can be adjusted according to the degree of affliction. Oral compositions can take the form of tablets, pills, capsules, semi-solids, powders, sustained release formulations, solutions, suspensions, elixirs, aerosols, or any other appropriate compositions.

The compositions are comprised of in general, a compound of formula (I) in combination with at least one pharmaceutically acceptable excipient. Such excipient may be any solid, liquid, semi-solid or, in the case of an aerosol composition, gaseous excipient that is generally available to one of skill in the art.

In general, in the case of oral or parenteral administration to adult humans weighing approximately 80 kg, a daily dose of preferably from about 10 mg to about 10,000 mg, more preferably from about 20 mg to about 1,000 mg, should be appropriate, although the upper limit may be exceeded when indicated. The daily dosage can be administered as singly dose or in separate doses, or for parenteral administration, it may be given as continuous infusion.

The compounds of this invention can be administered in combination with known anticancer agents or with other pharmaceutically active ingredients. Combinations of two or more pharmaceutically active ingredients may be administered in the form of a combination preparation containing a fixed dose of each of the pharmaceutically active ingredients or in the form of a combination of several pharmaceutical compositions each containing one of the pharmaceutically active ingredients.

Furthermore, the present invention relates to the compound of formula (I) as defined above for use in the treatment of inhibition of a disease being susceptible to the inhibition of the Hsp70 protein. Specific diseases which can be treated or inhibited by administration of the compound of formula (I) are cancer, in particular multiple myeloma, autoimmune disease, rheumatoid arthritis, inflammatory bowel disease and psoriasis.

The tetrahydroisoquinolin-1-one derivatives of the present invention can for example be synthesized via a reaction between homophthalic anhydride and imines as shown in Scheme 1 below. For this purpose a variety of imines can be produced in the first step. Besides the well-known reaction of amines and aldehydes in conventional organic solvents such as ethanol which can be utilized for the syntheses of 3a-c, a further procedure, using ethyl lactate as a solvent component, can be applied. By adding water to ethyl L-lactate the polarity of the resulting solvent can be adjusted for synthesizing aryl imines like 3d-h, which purely crystallize straight out of the solution in good yields.

Scheme 1. Reagents and conditions: (i) EtOH$_{abs}$, rt, 3 h; (ii) ethyl L-lactate/water (8:2 and 9:1, respectively), rt; (iii) TiCl$_4$, DIPEA, CH$_2$Cl$_{2abs}$, 0° C./rt, 3 h; (iv) CHCl$_{3abs}$, rt, 2 h; (v) NaHCO$_3$ (1M), EtOH, rt, 30 min; (vi) NaOH (8M), EtOH, rt, 30 min; (vii) H$_2$NR$^3$, i-butyl chloroformiate, NaHCO$_3$, CH$_3$CN$_{abs}$, 0° C./rt; (viii) H$_2$NR$^3$, TCBoc-chloride, NaHCO$_3$ and NEt$_3$, respectively, CH$_3$CN$_{abs}$, 0° C./rt; (ix) BBr$_3$, CH$_2$Cl$_{2abs}$, 0° C./rt. - The substitution pattern of compounds trans-7a-r is provided in Table 1.

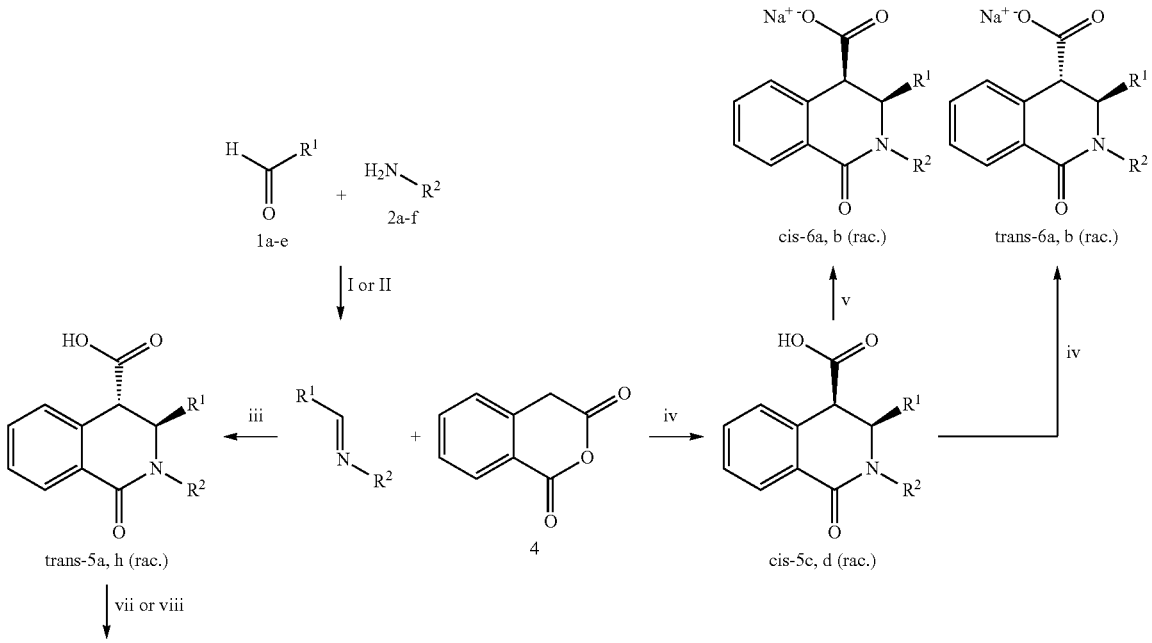

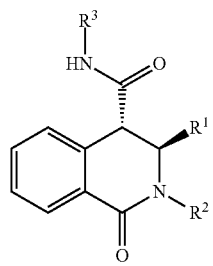

trans-7a-n, p-r (rac.)

trans-7d (rac.) ⎤
               ⎬ ix
trans-7o (rac.) ⎦

| | | |
|---|---|---|
| 1a $R^1$ = $C_6H_5$ | 2a $R^2$ = $C_6H_5$ | 3a, 5a $R^1$ = $R^2$ = $C_6H_5$ |
| 1b $R^1$ = p-($H_3$CO)—$C_6H_4$ | 2b $R^2$ = p-($H_3$CO)—$C_6H_4$ | 3b, 5b, 6b $R^1$ = p-($H_3$CO)—$C_6H_4$, $R^2$ = $C_6H_5$ |
| 1c $R^1$ = p-F—$C_6H_4$ | 2c $R^2$ = p-F—$C_6H_4$ | 3c, 5c, 6c $R^1$ = $C_6H_5$, $R^2$ = p-($H_3$CO)—$C_6H_4$ |
| 1d $R^1$ = p-Cl—$C_6H_4$ | 2d $R^2$ = p-Cl—$C_6H_4$ | 3d, 5d, 6d $R^1$ = $R^2$ = p-($H_3$CO)—$C_6H_4$ |
| 1e $R^1$ = 3,5-($H_3$C)$_2$—$C_6H_3$ | 2e $R^2$ = 3,5-($H_3$C)$_2$—$C_6H_3$ | 3e, 5e $R^1$ = $R^2$ = p-F—$C_6H_4$ |
| | 2f $R^2$ = p-($C_6H_5$O)$_2$—$C_6H_4$ | 3f, 5f $R^1$ = $R^2$ = p-Cl—$C_6H_4$ |
| | | 3g, 5g $R^1$ = $R^2$ = 3,5-($H_3$C)$_2$—$C_6H_3$ |
| | | 3h, 5h $R^1$ = p-($H_3$CO)—$C_6H_4$ |
| | | $R^2$ = p-($C_6H_5$O)—$C_6H_4$ |

Several methods for the synthesis of isoquinolone carboxylic acids out of homophthalic anhydride are known using e.g. Lewis acids, protic acids, bases, ionic liquids and heterogeneous catalysts in order to enhance stereoselectivity and yield. The direct conversion with imines bearing discriminating substituents is known to give the cis-diastereomer specifically. Hence, the synthesis of cis-5c and cis-5d can be carried out without further auxiliaries and results in good yield and selectivity (d.e. 96%). The trans-selective conversion (d.e. 96%) can be achieved by adding $TiCl_4$ and diisopropyl ethyl amine (DIPEA). Diastereomeric assignment can be accomplished by the coupling constant $J_{AB}$ of isoquinolone hydrogen H-3 and H-4, which is 5-6 Hz for the cis-isomer and 0-2 Hz for the trans-isomer.

The sodium salts trans-6b, cis-6c and cis-6d can be obtained via deprotonation with $NaHCO_3$. The known epimerization after treatment with NaOH can be utilized for the syntheses of the sodium salts trans-6c and trans-6d. The corresponding carboxamides can be synthesized via mixed anhydrides using i-butyl chloroformiate and 2,2,2-trichloro-1,1-dimethylethyl chloroformiate (TCBoc-chloride), respectively, followed by the in situ reaction with corresponding amines. Using TCBoc-chloride avoids the formation of isoquinolone carboxylester side-product, as no alcohol or other nucleophilic species is eliminated. The phenol trans-7o can be synthesized by cleaving both methoxy groups of trans-7d by means of $BBr_3$.

The compounds of the below examples and comparative examples including their effectivity in the inhibition of the Hsp70 protein as measured by the cell viability assay described below are summarized in the following Table 1.

TABLE 1

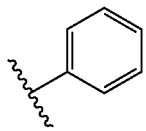 [SMILES: *c1ccccc1]

| Compd. | $R^1$ | $R^2$ | $R^3$ | INA-6 $EC_{50}$(±sdv) [μM]$^a$ |
|---|---|---|---|---|
| trans-5a | 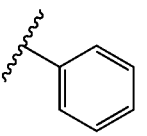 [SMILES: *c1ccccc1] | 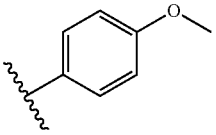 [SMILES: *c1ccc(OC)cc1] | —OH | 6.9 (±0.3) |
| trans-5b | 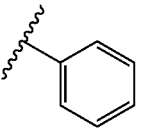 |  | —OH | 1.3 (±0.2) |

TABLE 1-continued

| Compd. | R¹ | R² | R³ | INA-6 EC$_{50}$(±sdv) [μM]$^a$ |
|---|---|---|---|---|
| cis-5c | phenyl | 4-methoxyphenyl | —OH | >100 |
| trans-5c | phenyl | 4-methoxyphenyl | —OH | 57 (±15) |
| cis-5d | 4-methoxyphenyl | 4-methoxyphenyl | —OH | >100 |
| trans-5d | 4-methoxyphenyl | 4-methoxyphenyl | —OH | 10.1 (±0.1) |
| trans-6b | 4-methoxyphenyl | phenyl | Na$^+$ O— | 2.0 (±0.1) |
| cis-6c | phenyl | 4-methoxyphenyl | Na$^+$ O— | >100 |
| trans-6c | phenyl | 4-methoxyphenyl | Na$^+$ O— | 64 (±19) |
| cis-6d | 4-methoxyphenyl | 4-methoxyphenyl | Na$^+$ O— | >100 |

TABLE 1-continued
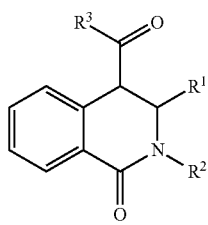
| Compd. | R¹ | R² | R³ | INA-6 EC$_{50}$(±sdv) [μM][a] |
|---|---|---|---|---|
| trans-6d | 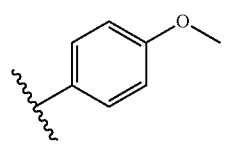 [SMILES: *c1ccc(OC)cc1] | 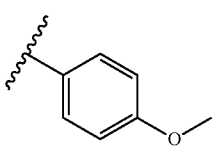 [SMILES: *c1ccc(OC)cc1] | Na$^+$–O— | 7.9 (±0.8) |
| trans-7a |  | 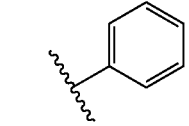 [SMILES: *c1ccccc1] | 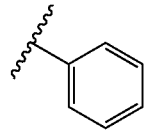 [SMILES: *c1ccccc1] | 2.3 (±0.6) |
| trans-7b | 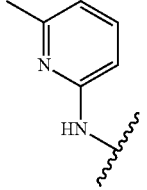 [SMILES: *Nc1cccc(C)n1] | 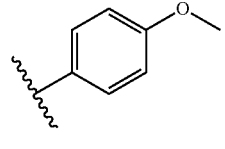 | 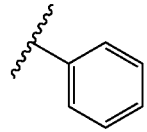 [SMILES: *c1ccccc1] | 0.41 (±0.03) |
| trans-7c | 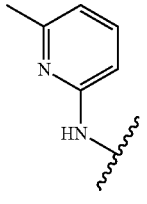 [SMILES: *Nc1cccc(C)n1] | 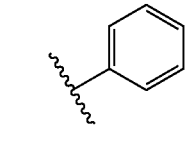 [SMILES: *c1ccccc1] | 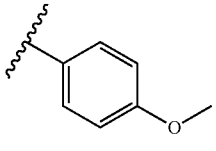 [SMILES: *c1ccc(OC)cc1] | —[b] |
| trans-7d | 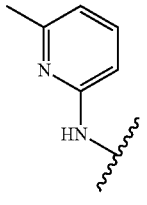 [SMILES: *Nc1cccc(C)n1] | 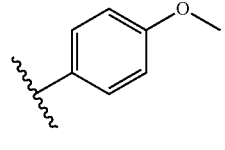 [SMILES: *c1ccc(OC)cc1] | 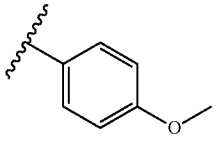 [SMILES: *c1ccc(OC)cc1] | 0.68 (±0.04) |
| trans-7e | 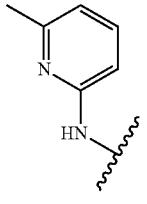 [SMILES: *Nc1cccc(C)n1] | 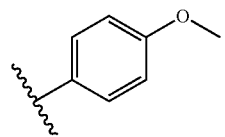 [SMILES: *c1ccc(OC)cc1] | 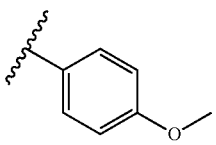 [SMILES: *c1ccc(OC)cc1] | 0.88 (±0.10) |

TABLE 1-continued
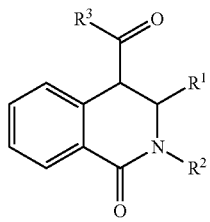
| Compd. | R¹ | R² | R³ | INA-6 EC$_{50}$(±sdv) [μM]$^a$ |
|---|---|---|---|---|
| trans-7f | 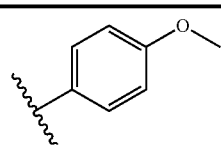 | 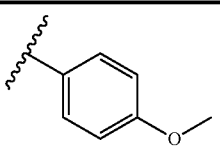 | 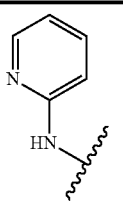 | 0.53 (±0.03) |
| trans-7g | 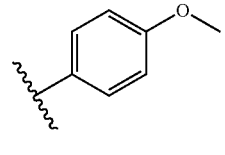 [SMILES: *c1ccc(OC)cc1] | 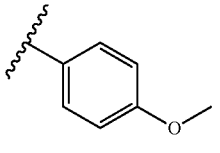 [SMILES: *c1ccc(OC)cc1] | 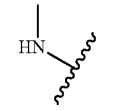 | 7.1 (±0.3) |
| trans-7h | 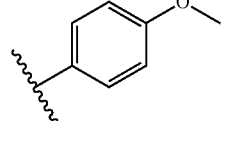 | 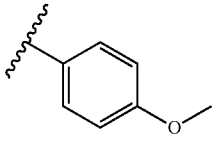 [SMILES: *c1ccc(OC)cc1] | 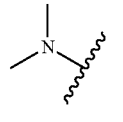 | >100 |
| trans-7i | 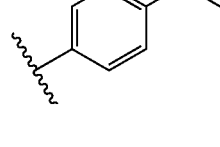 | 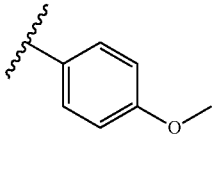 [SMILES: *c1ccc(OC)cc1] | 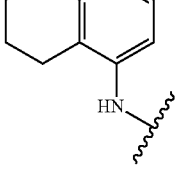 | >100 |
| trans-7j | 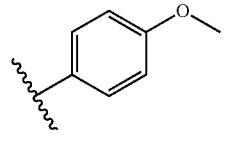 | 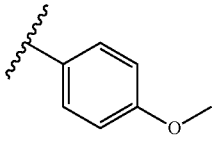 [SMILES: *c1ccc(OC)cc1] | 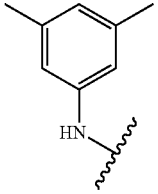 | 0.95 (±0.09) |
| trans-7k | 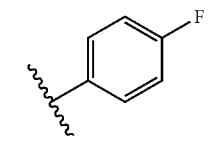 [SMILES: *c1ccc(F)cc1] | 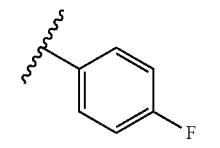 [SMILES: *c1ccc(F)cc1] | 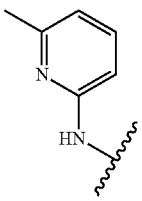 | 6.4 (±0.7) |
| trans-7l | 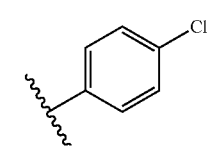 [SMILES: *c1ccc(Cl)cc1] | 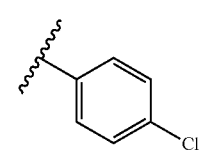 [SMILES: *c1ccc(Cl)cc1] | 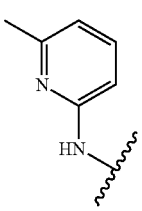 [SMILES: *Nc1cccc(C)n1] | 2.9 (±0.3) |

TABLE 1-continued

| Compd. | R¹ | R² | R³ | INA-6 EC$_{50}$(±sdv) [μM][a] |
|---|---|---|---|---|
| trans-7m | 3,5-dimethylphenyl | 3,5-dimethylphenyl | 6-methylpyridin-2-ylamino | 43 (±12)[b] |
| trans-7n | 4-methoxyphenyl | 4-phenoxyphenyl | 6-methylpyridin-2-ylamino | >100[b] |
| trans-7o | 4-hydroxyphenyl | 4-hydroxyphenyl | 6-methylpyridin-2-ylamino | 30 (±2) |
| trans-7p | 4-methoxyphenyl | phenyl | pyrimidin-2-ylamino | 0.20 (±0.01) |
| trans-7q | 4-methoxyphenyl | phenyl | pyridin-3-ylamino | 0.57 (±0.02) |
| trans-7r | 4-methoxyphenyl | phenyl | 4,6-dimethylpyridin-2-ylamino | 0.34 (±0.04) |

[a] All EC50 values are the mean of at least three determinations
[b] Precipitated under assay-conditions The data in the above table demonstrate that replacing the prior art substituents in position 4 of the tetrahydroisoquinolin-1-one derivatives by the substituents according to the invention significantly lowers the $EC_{50}$ values of the compounds thereby indicating an increased effectivity in the inhibition of the Hsp70 protein. If, for example, the $R^3$ substituent —OH in compound trans-5a is replaced by a methylpyridinylamino substituent in the compound trans-7a, the $EC_{50}$ value decreases from 6.9 to 2.3 µM. Similarly, if in compound trans-5b the —OH substituent for $R^3$ is replaced by methylpyridinylamino in compound trans-7b, the $EC_{50}$ value decreases from 1.3 to 0.41 µM. A further example is compound trans-5d which bears a —OH substituent as $R^3$ (and which therefore is not according to the invention) and which exhibits a $EC_{50}$ value of 10.1 µM. Replacing the —OH substituent by methylpyridinylamino (trans-7d), methylphenylamino (trans-7e) and pyridinylamino (trans-7f) results in a decrease in the $EC_{50}$ value to 0.68, 0.88 and 0.53 µM, respectively. On the other hand, amino substituents for $R^3$ which are not according to the invention result in compounds having significantly increased $EC_{50}$ values of 7.1 µM (trans-7g) and above 100 µM (trans-7h and trans-7i).

Cell Viability Assay

The effect of pharmacological Hsp70 inhibition on cell viability was analyzed after 72 hours of treatment in both non-malignant (mononuclear cells from the peripheral blood) and malignant lymphocytes (multiple myeloma cells). The mononuclear cells were separated from the peripheral blood of healthy donors by Ficoll-Hypaque density gradient centrifugation. The human cell line INA-6 represents a well-established model for multiple myeloma. The percentage of viable and apoptotic cell fractions was assessed using an annexin V-FITC/propidium iodide (PI) staining kit (Bender MedSystems, Vienna, Austria) according to manufacturer's instructions. In brief, cells were washed in PBS, incubated for 10 min in 100 ml binding buffer (10 mM HEPES/NaOH, pH 7.4, 140 mM NaCl, 2.5 mM $CaCl_2$) containing 2.5 ml annexin V-FITC mix and 1 mg/ml propidium iodide (PI), subsequently diluted with 100 ml binding buffer and analyzed by flow cytometry (FACSCalibur/CELLQuest; Becton Dickinson, Heidelberg, Germany). Whereas viable cells are negative for both, annexin V-FITC and PI, early apoptotic cells show a positive annexin V-FITC staining, and cells in a late apoptotic stage which lose their membrane integrity additionally incorporate DNA-binding PI. To establish kill curves, concentrations of the tested compounds were titrated, and the measured viable cell fractions were further analyzed using the Prism Calculation Software (GraphPad Software Inc., La Jolla, USA).

Apoptosis Assays. Hsp70-dependent prevention of apoptosis was investigated by analyses of the apoptosis-inducing factors (AIF) and of the caspases 9 and 3 in INA-6 cells. INA-6 cells were treated with 0.6 µM of compound trans-7b for 8 hours prior to analyze nuclear translocation of AIF. Staining of the nuclear protein lamin A was used as a loading control. Upon treatment of INA-6 cells with 0.6 µM of compound trans-7b for 24 hours cleavage and activation of the caspases 9 and 3 were analyzed by Western. Analysis of cleavage of the bona fide caspase substrate PARP served as a control for caspase activation. Co-treatment with the pan-caspase inhibitor Z-VAD-FMK (50 µM) was employed as another specificity control.

Western Blot Analysis. Protein expression levels were determined with Western blotting procedures (M. Chatterjee, et al., Blood 2002, 100, 3311-3318). Following separation by SDS-PAGE, proteins were transferred onto nitrocellulose membranes (Schleicher & Schuell, Dassel, Germany) and stained with antibodies against Hsp72, Hsp73, Hsp90 (all from Enzo Life Science, Lörrach, Germany), AIF, lamin A, caspases 9 and 3, PARP (all from Santa Cruz, Heidelberg, Germany). An anti-α tubulin antibody (Sigma, Deisenhofen, Germany) was employed to assess equal loading. Secondary antibodies used were anti-rat (Enzo Life Science), anti-rabbit and anti-mouse (both from GE Healthcare, Little Chalfont, UK). As demonstrated by the data in FIGS. 1A to 1C, trans-7b treatment decreases HSP72 and HSP73 but not HSP90 expression, and inhibits HSP70/HSP90 multi-chaperone activity leading to downregulation of constitutive expression levels of well-defined HSP70-dependent client proteins in myeloma cells. The heat shock proteins HSP72 and HSP73 critically interact with HSP90 in order to mediate an essential chaperone function for a multitude of proteins including various signaling intermediates. According to an established HSP72/73-dependent client protein signature and its role for survival in MM, the proposed anti-HSP72/73 effect of trans-7b in the INA-6 multiple myeloma (MM) cell line model was evaluated. INA-6 cells were incubated either with DMSO as a solvent control or with the compound trans-7b (0.6 µM), and additionally incubated with the pan-caspase inhibitor Z-VAD-FMK (50 µM) prior to Western blot analyses of HSP72, HSP73 or HSP90 expression (FIG. 1A), of the expression of several well-defined HSP70/HSP90 chaperon-dependent signaling intermediates or their substrates (FIG. 1B), or of the HSP70-dependent nuclear translocation of the apoptosis-inducing factor (AIF) (FIG. 1C). For Western analyses either whole cell pellets (FIGS. 1A and 1B) or nuclear pellets (FIG. 1C) were dissolved in lysis buffer (20 mM HEPES (pH 7.9), 350 mM NaCl, 1 mM $MgCl_2$, 0.5 mM EDTA, 0.1 mM EGTA, 1% NP40, 0.5 mM dithiothreiol (DTT), 1 mM $Na_3VO_4$, 0.1 mM PMSF and 1 µg/ml aprotinin). Lysates were cleared by centrifugation, measured by quantitative protein assay (Bio-Rad, München, Germany) and subjected to SDS gel electrophoresis. Proteins were transferred onto nitrocellulose membranes (Schleicher & Schuell, Dassel, Germany), incubated with primary antibodies against HSP72, HSP73, HSP90 (from Stressgen Bioreagents, Ann Arbor, USA), AKT, C-Raf, RIP, IKKα, p-MEK, MEK, p-ERK, ERK, p-STAT3, STAT3, AIF (from Cell Signaling Technology, Frankfurt a.Main, Germany), Lamin A, β-actin (from Sigma-Aldrich, Deisenhofen, Germany), or α-tubulin (from Biozol Eching, Germany) according to standard procedures and visualized with secondary anti-rabbit horseradish peroxidase (HRP)-conjugated antibodies using an enhanced chemoluminescence detection system (ECL, Amersham, Freiburg, Germany). The WB analyses show that in contrast to HSP90 (and α-tubulin which was stained as a loading control), the constitutive expression level of the major HSP70 isoforms HSP72 and HSP73 are reduced indicating their binding to trans-7b and their subsequent degradation (FIG. 1A). In addition, reduced expression levels of a multitude of signaling proteins, which have been shown to be dependent on the HSP70/HSP90 multi-chaperone function, have been observed. Thus, AKT, C-Raf, RIP, IKKα and MEK levels were strongly downregulated after trans-7b treatment. Likewise, p-MEK as a Raf substrate, p-ERK as a MEK substrate as well as pSTAT3 as a janus kinase substrate are downregulated (FIG. 1B). Because HSP90 expression remains unchanged (FIG. 1A), these results clearly show that trans-7b disrupts HSP70-mediated chaperone function. In addition to signaling intermediates, the apoptosis-inducing factor (AIF), which is a pro-apoptotic factor that is physiologically inactive through HSP70 binding, was analyzed upon treatment with trans-7b. Western analyses revealed that activated AIF was shifting from the cytosol to the nucleus 8 hours after trans-7b treatment. This finding indicates that binding of HSP70 to AIF is prevented by trans-7b.

Figure 2:
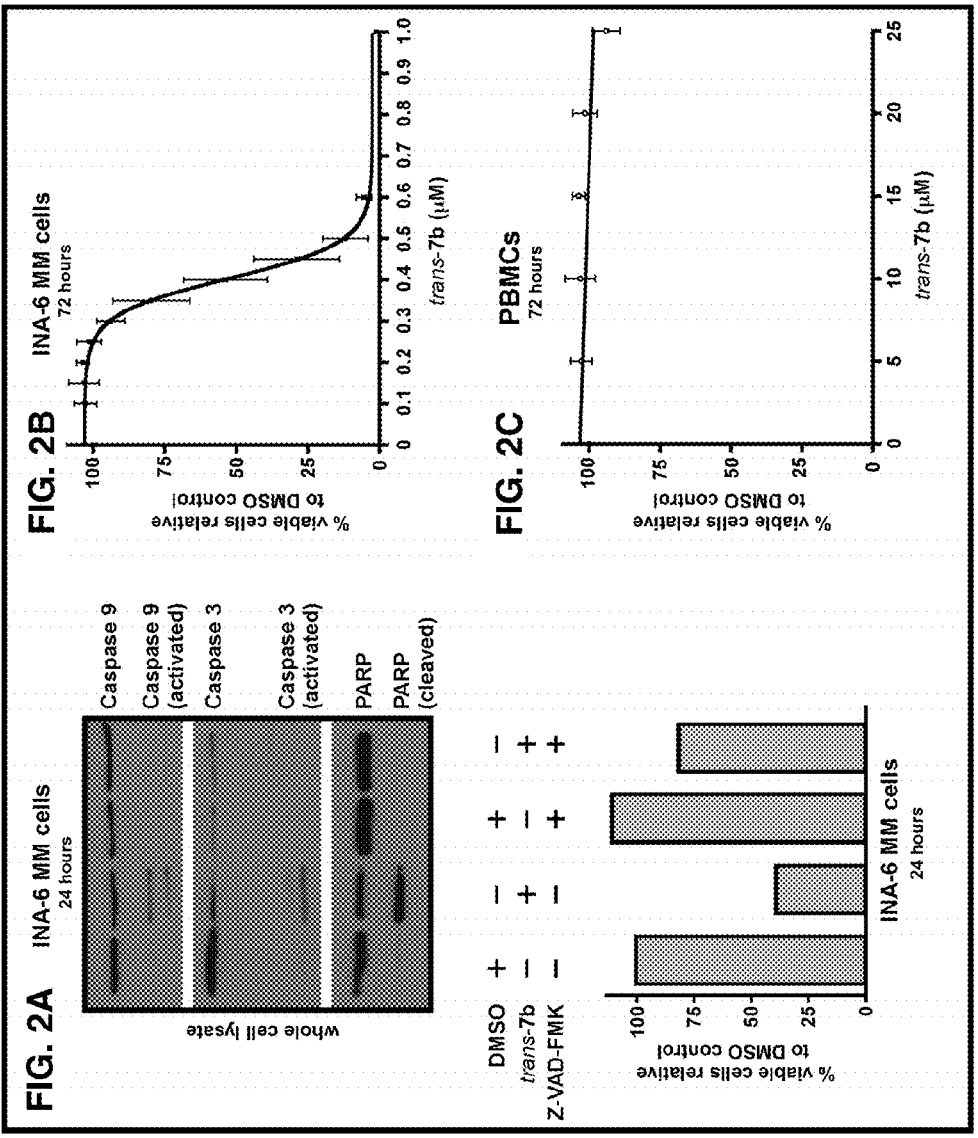
FIG. 2A depicts the results of Western blot analyses of caspases 9 and 3, and the caspase substrate PARP (upper panel), and viability analyses (lower panel) of INA-6 MM cells upon treatment with trans-7b for 24 hours.
FIGS. 2B and 2C depicts the results of viability analyses of INA-6 MM cells (FIG. 2B) in comparison with non-malignant PBMCs (FIG. 2C).

As demonstrated by the data in FIGS. 2A to 2C, trans-7b treatment leads to activation of the caspases 9 and 3, and induction of apoptosis in malignant INA-6 MM cells but not in non-malignant peripheral blood mononuclear cells (PBMCs). In FIG. 2A Western blot analyses of caspases 9 and 3, and the caspase substrate PARP (upper panel), and viability analyses (lower panel) of INA-6 MM cells upon treatment with trans-7b for 24 hours are shown. INA-6 cells were either incubated with DMSO (as a solvent control) or with 0.6 µM of trans-7b, and additionally incubated either with DMSO or the pan-caspase inhibitor Z-VAD-FMK prior to analyses by Western or viability assessment (without Z-VAD-FMK co-treatment) by Annexin V/propidum iodide double staining. For Western analyses INA-6 cell pellets were dissolved in lysis buffer (20 mM HEPES (pH 7.9), 350 mM NaCl, 1 mM $MgCl_2$, 0.5 mM EDTA, 0.1 mM EGTA, 1% NP40, 0.5 mM dithiothreiol (DTT), 1 mM $Na_3VO_4$, 0.1 mM PMSF and 1 µg/ml aprotinin). Lysates were cleared by centrifugation, measured by quantitative protein assay (Bio-Rad, München, Germany) and subjected to SDS gel electrophoresis. Proteins were transferred onto nitrocellulose membranes (Schleicher & Schuell, Dassel, Germany), incubated with antibodies specific for caspase 9, caspase 3 or PARP (Cell Signaling Technology, Frankfurt a.Main, Germany) according to standard procedures and visualized with secondary anti-rabbit horseradish peroxidase (HRP)-conjugated antibodies using an enhanced chemoluminescence detection system (ECL, Amersham, Freiburg, Germany). Western analyses reveal sequential caspase 9 and 3 cleavage leading to their activation as indicated by specific PARP cleavage. Annexin V/propidium iodide (PI) staining was performed using a fluorescein isothiocyanate (FITC) conjugated recombinant human annexin/propidium iodide kit (BenderMedSystems, Vienna, Austria) according to the manufacturer's instructions. INA-6 cells were washed in PBS, incubated for 15 minutes in 100 ml binding buffer (10 mM HEPES/NaOH, pH 7.4, 140 mM NaCl, 2.5 mM $CaCl_2$) containing 2.5 mL annexin V-FITC mix and 1 mg/ml PI and analyzed by flow cytometry (FACSCalibur/CELLQuest; Becton Dickinson, Heidelberg, Germany). Whereas early apoptosis is characterized by positive annexin V-FITC staining reaction, cells in a late apoptotic stage lose their membrane integrity and additionally incorporate PI. Thus, the fraction of viable cells remains negative for both annexin V-FITC and PI. In comparison with the DMSO control (100%) viability of trans-7b-treated INA-6 cells were drastically decreased. In contrast, if INA-6 MM cells were concomitantly incubated with the pan-caspase inhibitor Z-VAD-FMK (50 µM), which sufficiently inhibited caspase activation and PARP cleavage, induction of apoptosis was largely prevented indicating that trans-7b-induced apoptosis is specifically dependent on caspase activation. Based on the above described experiments also viability analyses of INA-6 in comparison with non-malignant PBMCs were performed choosing a longer incubation time (72 hours) as shown in FIG. 2B or C. Raw data of three independent experiments have been calculated to establish means, standard deviation and dose-effect curves of trans-7b. The resulting experimental data show that INA-6 tumor cells are highly sensitive (in a low micromolar range) towards trans-7b treatment, whereas primary PBMCs lack any cytotoxic effect even in higher micromolar concentrations.

Figure 3:
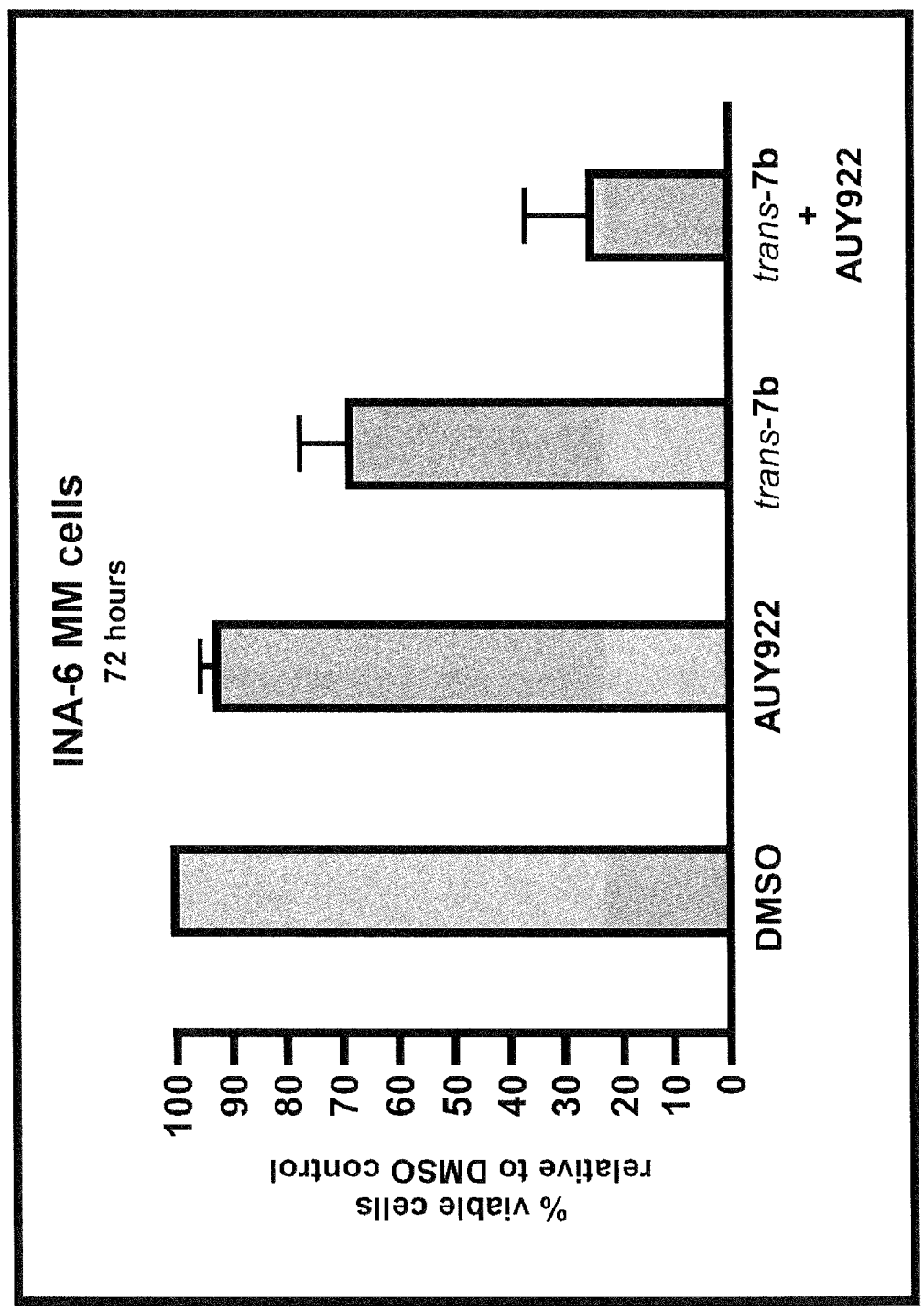
FIG. 3 depicts the effects of a concomitant treatment of trans-7b with the HSP90 inhibitor NVP-AUY922 on the viability of INA-6 cells incubated with DMSO (as a solvent control), sublethal concentrations of AUY922 (7.5 nM), trans-7b (3.5 µM) or a combination of both.
m

The data in FIG. 3 shows that concomitant inhibition of HSP72/73 by trans-7b strongly enhanced the apoptotic effect of the HSP90 inhibitor NVP-AUY922. The heat shock protein HSP90, which critically cooperates with HSP72 and HSP73 to mediate a chaperone function for a multitude of proteins, is regarded as a reasonable therapeutic target in MM. Synergistic effects of a combinatorial HSP90/HSP70 inhibition in MM were recently demonstrated. Therefore, potential effects of a concomitant treatment of trans-7b with the HSP90 inhibitor NVP-AUY922 on viability of INA-6 cells were analyzed. INA-6 cells were incubated either with DMSO (as a solvent control), sublethal concentrations of AUY922 (7.5 nM) or trans-7b (3.5 µM) or with a combination of both. Viability was measured by Annexin V-FITC/propidium iodide double staining (BenderMedSystems, Vienna, Austria) according to the manufacturer's instructions. Cells were washed in PBS, incubated for 15 minutes in 100 ml binding buffer (10 mM HEPES/NaOH, pH 7.4, 140 mM NaCl, 2.5 mM $CaCl_2$) containing 2.5 mL annexin V-FITC mix and 1 mg/ml PI and analyzed by flow cytometry (FACSCalibur/CELLQuest; Becton Dickinson, Heidelberg, Germany). Whereas early apoptosis is characterized by positive annexin V-FITC staining reaction, cells in a late apoptotic stage lose their membrane integrity and additionally incorporate PI. Thus, the fraction of viable cells remains negative for both annexin V-FITC and PI. Raw data of three independent measurements were set in relation to their respective DMSO controls, and means and standard deviations were calculated using the Graphpad Prism software (Graphpad, La Jolla, USA). The experimental data clearly show that treatment with the HSP72/73 inhibitor trans-7b strongly enhanced the apoptotic effect of the HSP90 inhibitor NVP-AUY922.

General Procedures for the Syntheses of the Imines

Method A: To a solution of the aniline derivative (1 eq) in abs. ethanol the corresponding aldehyde (1 eq) was added and stirred for 3 h at room temperature. The solvent was evaporated and the crude product was purified by crystallization (3a-c). Method B: The aniline derivative (1 eq) was dissolved in a mixture of ethyl L-lactate and water, and the corresponding aldehyde (1 eq) was added. The solution was stirred till all compounds were dissolved. The immediately formed crystals were filtered, washed with cold water and dried in vacuo to give the product. (3d-h)

General Procedure for the Syntheses of the cis-isoquinolone carboxylic Acids (cis-5c-d)

To a solution of an imine (1 eq) in abs. chloroform homophthalic anhydride (1 eq) was added under Ar atmosphere and stirred for 2 h at room temperature. The formed precipitate was filtered and the crude purified by crystallization.

General Procedure for the Syntheses of the trans-isoquinolone carboxylic acids (trans-5a-h)

Homophthalic anhydride (1 eq) was dissolved in abs. dichloromethane under Ar atmosphere. The solution was cooled to 0° C. and $TiCl_4$ (1 eq) was added under stirring. After 5 min N,N-diisopropylethylamine (1 eq) was added and the solution was stirred for 30 min. The corresponding imine dissolved in dichloromethane (1.5 eq) was added dropwise at 0° C. The reaction mixture was allowed to warm to room temperature and stirred for 3 h. The solvent was evaporated and the crude product was purified by column chromatography (silica gel 60, first eluent chloroform/ethanol/formic acid 10:0.3:0.1, second eluent chloroform/ethyl acetate/n-hexane/formic acid 7:5:0.25:0.05, and third eluent petroleum ether/ethyl acetate/formic acid 3:2:0.02 if necessary).

General Procedure for the Syntheses of the trans-1,2,3,4-tetrahydroisoquinoline-4-carboxamides (trans-7a-n, p-r)

The respective 1-oxo-1,2,3,4-tetrahydroisoquinoline-4-carboxylic acid (1 eq) was dissolved in abs. acetonitrile (5 mL) under Ar atmosphere and cooled to 0° C. Either solid NaHCO$_3$ or NEt$_3$ was added. Afterwards 1.5 eq of i-butyl chloroformiate and 2,2,2-trichloro-1,1-dimethylethyl chloroformiate, respectively, was added. The mixture was stirred for 30 min at 0° C., the corresponding amine (1.5 eq) was added, and the solution was stirred for additional 2 h while the mixture was allowed to warm-up to room temperature.

Using the above general procedures the following compounds were prepared as comparative examples and examples according to the invention. These examples are intended as being illustrative only and should not be construed as limiting.

COMPARATIVE EXAMPLE 1 trans-2,3-Diphenyl-1-oxo-1,2,3,4-tetrahydroisoquinoline-4-carboxylic acid (trans-5a): Homophthalic anhydride (15 mmol, 2.4 g), N,N-diisopropylethylamine (15 mmol, 2.6 mL), titanium tetrachloride (15 mmol, 1.7 mL), 3a (22.5 mmol, 4.1 g); yield: 41% (47%), colorless solid; mp: 226-229° C.

COMPARATIVE EXAMPLE 2 trans-3-(4-Methoxyphenyl)-1-oxo-2-phenyl-1,2,3,4-tetrahydroisoquinoline-4-carboxylic acid (trans-5b): Homophthalic anhydride (15 mmol, 2.4 g), N,N-diisopropylethylamine (15 mmol, 2.6 mL), titanium tetrachloride (15 mmol, 1.7 mL), 3b (22.5 mmol, 4.8 g); yield: 44%; colorless solid; mp: 171-173° C.

COMPARATIVE EXAMPLE 3 cis-2-(4-Methoxyphenyl)-1-oxo-3-phenyl-1,2,3,4-tetrahydroisoquinoline-4-carboxylic acid (cis-5c): Homophthalic anhydride (40 mmol, 6.5 g), 3c (60 mmol, 12.7 g); the crude product was purified by crystallization from ethyl acetate. Yield: 48% (91%); colorless solid; mp: 208-209° C.

COMPARATIVE EXAMPLE 4 trans-2-(4-Methoxyphenyl)-1-oxo-3-phenyl-1,2,3,4-tetrahydroisoquinoline-4-carboxylic acid (trans-5c): Homophthalic anhydride (31 mmol, 5.0 g), N,N-diisopropylethylamine (31 mmol, 5.3 mL), titanium tetrachloride (31 mmol, 3.4 mL), 3c (46 mmol, 9.8 g); yield: 44% (63%); colorless amorphous solid; mp: 106-118° C.

COMPARATIVE EXAMPLE 5 cis-2,3-Bis(4-methoxyphenyl)-1-oxo-1,2,3,4-tetrahydroisoquinoline-4-carboxylic acid (cis-5d): Homophthalic anhydride (30 mmol, 4.9 g), 3d (30 mmol, 7.2 g); the crude product was purified by crystallization from ethanol. Yield: 44%; colorless solid; mp: 232-233° C.

COMPARATIVE EXAMPLE 6 trans-2,3-Bis(4-methoxyphenyl)-1-oxo-1,2,3,4-tetrahydroisoquinoline-4-carboxylic acid (trans-5d): Homophthalic anhydride (19 mmol, 3.1 g), N,N-diisopropylethylamine (19 mmol, 3.2 mL), titanium tetrachloride (19 mmol, 2.1 mL), 3d (28 mmol, 6.8 g); yield: 47%; colorless solid; mp: 201-203° C.

COMPARATIVE EXAMPLE 7 trans-2,3-Bis(4-fluorophenyl)-1-oxo-1,2,3,4-tetrahydroisoquinoline-4-carboxylic acid (trans-5e): Homophthalic anhydride (13 mmol, 2.2 g), N,N-diisopropylethylamine (13 mmol, 2.3 mL), titanium tetrachloride (13 mmol, 1.5 mL), 3e (16 mmol, 3.5 g); yield: 49%; colorless amorphous solid; mp: 116-118° C.

COMPARATIVE EXAMPLE 8 trans-2,3-Bis(4-chlorophenyl)-1-oxo-1,2,3,4-tetrahydroisoquinoline-4-carboxylic acid (trans-5f): Homophthalic anhydride (9 mmol, 1.5 g), N,N-diisopropylethylamine (9 mmol, 1.6 mL), titanium tetrachloride (9 mmol, 1.0 mL), 3f (11 mmol, 2.8 g); yield: 39%; colorless amorphous solid; mp: 116-127° C.

COMPARATIVE EXAMPLE 9 trans-2,3-Bis(3,5-dimethylphenyl)-1-oxo-1,2,3,4-tetrahydroisoquinoline-4-carboxylic acid (trans-5g): Homophthalic anhydride (11 mmol, 1.8 g), 3g (13.5 mmol, 3.2 g); the crude product was dissolved in acetonitrile and crystallization initiated by adding petroleum ether to give pure trans-5g. Yield: 58%; colorless solid; mp: 269-271° C.

COMPARATIVE EXAMPLE 10 trans-3-(4-Methoxyphenyl)-1-oxo-2-(4-phenoxyphenyl)-1,2,3,4-tetrahydroisoquinoline-4-carboxylic acid (trans-5h): Homophthalic anhydride (8 mmol, 1.3 g), N,N-diisopropylethylamine (8 mmol, 1.4 mL), titanium tetrachloride (8 mmol, 0.9 mL), 3h (10 mmol, 3.0 g); yield: 46%; colorless amorphous solid; mp: 109-115° C.

COMPARATIVE EXAMPLE 11

Sodium trans-3-(4-methoxyphenyl)-1-oxo-2-phenyl-1,2,3,4-tetrahydroisoquinoline-4-carboxylate (trans-6b): Compound trans-5b (0.4 mmol, 150 mg) was suspended in ethanol and a solution of NaHCO$_3$ (0.4 mmol, 400 µL, 1M) was added. After stirring for 30 min at room temperature the solvent was evaporated to give pure trans-6b. Yield: 96%; colorless solid; mp: 97-99° C.

COMPARATIVE EXAMPLE 12

Sodium cis-2-(4-methoxyphenyl)-1-oxo-3-phenyl-1,2,3,4-tetrahydroisoquinoline-4-carboxylate (cis-6c): Compound cis-5c (0.5 mmol, 200 mg) was suspended in ethanol and a solution of NaHCO$_3$ (0.5 mmol, 540 µL, 1M) was added. After stirring for 30 min at room temperature the solvent was evaporated to give pure cis-6c. Yield: 98%; colorless solid; mp: 234-236° C.

COMPARATIVE EXAMPLE 13

Sodium trans-2-(4-methoxyphenyl)-1-oxo-3-phenyl-1,2,3,4-tetrahydroisoquinoline-4-carboxylate (trans-6c): Compound cis-5c (0.5 mmol, 200 mg) was suspended in ethanol and a solution of NaOH (0.5 mmol, 70 µL, 8M) was added.

After stirring for 30 min at room temperature the solvent was evaporated to give pure trans-6c. Yield: 97%; colorless solid; mp: 207-209° C.

COMPARATIVE EXAMPLE 14

Sodium trans-2,3-bis(4-methoxyphenyl)-1-oxo-1,2,3,4-tetrahydroisoquinoline-4-carboxylate (cis-6d): Compound cis-5d (0.5 mmol, 200 mg) was suspended in ethanol and a solution of NaHCO$_3$ (0.5 mmol, 500 µL, 1M) was added. After stirring for 30 min at room temperature the solvent was evaporated to give pure cis-6d. Yield: 98%; colorless solid; mp: 208-209° C.

COMPARATIVE EXAMPLE 15

Sodium cis-2,3-bis(4-methoxyphenyl)-1-oxo-1,2,3,4-tetrahydroisoquinoline-4-carboxylate (trans-6d): Compound cis-5d (1 mmol, 400 mg) was suspended in ethanol and a solution of NaOH (1 mmol, 125 µL, 8M) was added. After stirring for 30 min at room temperature the solvent was evaporated. The residue was dissolved in acetone and crystallization initiated by adding diethyl ether to give pure trans-6d. Yield: 89%; colorless solid; mp: 216-218° C.

EXAMPLE 1 trans-N-(6-Methyl pyridin-2-yl)-1-oxo-2,3-diphenyl-1,2,3,4-tetrahydroisoquinoline-4-carboxamide (trans-7a): Quantities: trans-5a (0.9 mmol, 300 mg), NaHCO$_3$ (0.9 mmol, 75 mg), 2,2,2-trichloro-1,1-dimethylethyl chloroformiate (1.3 mmol, 315 mg) and 2-amino-6-picoline (1.3 mmol, 135 µL). The precipitate was filtered, suspended in water and dried in vacuo. Yield: 82%; colorless solid; mp: 265-266° C.

EXAMPLE 2 trans-3-(4-Methoxyphenyl)-N-(6-methylpyridin-2-yl)-1-oxo-2-phenyl-1,2,3,4-tetrahydroisoquinoline-4-carboxamide (trans-7b): Quantities: trans-5b (1 mmol, 375 mg), NaHCO$_3$ (2 mmol, 170 mg), i-butyl chloroformiate (1.5 mmol, 195 µL) and 2-amino-6-picoline (1.5 mmol, 150 µL). The precipitate was filtered and extracted with CHCl$_3$ using a soxhlet extractor. The resulting organic phase was evaporated. Crystallization from ethyl acetate and toluene gave trans-7b. Yield: 55%; colorless solid; mp: 265-268° C.

EXAMPLE 3 trans-2-(4-Methoxyphenyl)-N-(6-methylpyridin-2-yl)-1-oxo-3-phenyl-1,2,3,4-tetrahydroisoquinoline-4-carboxamide (trans-7c): Quantities: trans-5c (2 mmol, 750 mg), NaHCO$_3$ (4 mmol, 335 mg), i-butyl chloroformiate (3 mmol, 390 µL) and 2-amino-6-picoline (3 mmol, 305 µL). The precipitate was filtered and extracted with CHCl$_3$ using a soxhlet extractor. The obtained organic phase was evaporated. Crystallization from ethyl acetate gave trans-7c. Yield: 54%; colorless solid; mp: 284-286° C.

EXAMPLE 4 trans-2,3-Bis(4-methoxyphenyl)-N-(6-methylpyridin-2-yl)-1-oxo-1,2,3,4-tetrahydroisoquinoline-4-carboxamide (trans-7d): Quantities: trans-5d (3.5 mmol, 1.4 g), NaHCO$_3$ (7 mmol, 585 mg), 2,2,2-trichloro-1,1-dimethylethyl chloroformiate (5.2 mmol, 1.25 g) and 2-amino-6-picoline (5.2 mmol, 525 µL). The precipitate was filtered and extracted with CHCl$_3$ using a soxhlet extractor. The obtained organic phase was evaporated. Crystallization from MeOH gave trans-7d. Yield: 71%; colorless solid; mp: 252-254° C.

EXAMPLE 5 trans-2,3-Bis(4-methoxyphenyl)-1-oxo-N-(m-tolyl)-1,2,3,4-tetrahydroisoquinoline-4-carboxamide (trans-7e): Quantities: trans-5d (2 mmol, 810 mg), NaHCO$_3$ (4 mmol, 335 mg), i-butyl chloroformiate (3 mmol, 390 µL) and m-toluidine (3 mmol, 320 µL). The reaction mixture was evaporated, dissolved in CHCl$_3$ and extracted with aqueous formic acid (5%). The organic layer was dried over Na$_2$SO$_4$, concentrated in vacuo to a few mL and trans-7e was precipitated by adding Et$_2$O. Yield: 64%; colorless solid; mp: 254-256° C.

EXAMPLE 6 trans-2,3-Bis(4-methoxyphenyl)-1-oxo-N-(pyridin-2-yl)-1,2,3,4-tetrahydroisoquinoline-4-carboxamide (trans-7f): Quantities: trans-5d (2 mmol, 810 mg), NaHCO$_3$ (4 mmol, 335 mg), i-butyl chloroformiate (3 mmol, 390 µL) and 2-aminopyridine (3 mmol, 280 mg). The precipitate was filtered, dissolved in CHCl$_3$ and extracted with water. The organic layer was dried over Na$_2$SO$_4$ and concentrated in vacuo. Crystallization from ethyl acetate gave trans-7f. Yield: 62%; colorless solid; mp: 219-229° C.

COMPARATIVE EXAMPLE 16 trans-2,3-Bis(4-methoxyphenyl)-N-methyl-1-oxo-1,2,3,4-tetrahydroisoquinoline-4-carboxamide (trans-7g): Quantities: trans-5d (1.2 mmol, 500 mg), NaHCO$_3$ (1.2 mmol, 105 mg), 2,2,2-trichloro-1,1-dimethylethyl chloroformiate (1.9 mmol, 445 mg) and methylamine (1.9 mmol, 0.9 µL, 2M in THF). The solvent was reduced in vacuo and the residue was purified by column chromatography (silica gel 60, n-hexane/ethyl acetate/formic acid 1:2:0.1) and crystallized from ethyl acetate to give trans-7g. Yield: 74%; colorless solid; mp: 202-203° C.

COMPARATIVE EXAMPLE 17 trans-2,3-Bis(4-methoxyphenyl)-N,N-dimethyl-1-oxo-1,2,3,4-tetrahydroisoquinoline-4-carboxamide (trans-7h): Quantities: trans-5d (1.0 mmol, 400 mg), NEt$_3$ (1.0 mmol, 140 µL), 2,2,2-trichloro-1,1-dimethylethyl chloroformiate (1.5 mmol, 360 mg) and dimethylamine (2.0 mmol, 1.0 mL, 2M in THF). The solvent was reduced in vacuo and the residue was purified by column chromatography (silica gel 60, $1^{st}$ n-hexane/ethyl acetate/formic acid 1:10:0.1 and $2^{nd}$ chloroform/ethanol 1 0:0.5) to give trans-7h. Yield: 90%; colorless amorphous solid; mp: 105-107° C.

COMPARATIVE EXAMPLE 18 trans-2,3-Bis(4-methoxyphenyl)-1-oxo-N-(5,6,7,8-tetrahydronaphthalen-1-yl)-1,2,3,4-tetrahydroisoquinoline-4-carboxamide (trans-7i): Quantities: trans-5d (1.2 mmol, 500 mg), NEt$_3$ (1.2 mmol, 175 µL), 2,2,2-trichloro-1,1-dimethylethyl chloroformiate (1.9 mmol, 445 mg) and 5,6,7,8-tetrahydro-1-naphthylamine (1.9 mmol, 260 ML). The reaction mixture was concentrated in vacuo, dissolved in CHCl$_3$ and extracted with aqueous formic acid (5%). The organic layer was dried over Na$_2$SO$_4$ and evaporated. Crystallization from ethyl acetate gave trans-7i. Yield: 63%; colorless solid; mp: 131-133° C.

EXAMPLE 7 trans-N-(3,5-Dimethylphenyl)-2,3-bis(4-methoxyphenyl)-1-oxo-1,2,3,4-tetrahydroisoquinoline-4-carboxamide (trans-7j): Quantities: trans-5d (1.2 mmol, 500 mg), NEt$_3$ (1.2 mmol, 175 µL), 2,2,2-trichloro-1,1-dimethylethyl chloroformiate (1.9 mmol, 445 mg) and 3,5-dimethylaniline (1.9 mmol, 230 µL). The precipitate was filtered, dissolved in CHCl$_3$ and extracted with aqueous formic acid (5%). The organic layer was dried over Na$_2$SO$_4$ and evaporated to give trans-7j. Yield: 91%; colorless solid; mp: 286-288° C.

EXAMPLE 8 trans-2,3-Bis(4-fluorophenyl)-N-(6-methylpyridin-2-yl)-1-oxo-1,2,3,4-tetrahydroisoquinoline-4-carboxamide (trans-7k): Quantities: trans-5e (1.3 mmol, 500 mg), NEt$_3$ (1.3 mmol, 185 µL), 2,2,2-trichloro-1,1-dimethylethyl chloroformiate (2.0 mmol, 475 mg) and 2-amino-6-picoline (2.0 mmol, 200 µL). The precipitate was filtered and crystallized from CHCl$_3$ to give trans-7k. Yield: 90%; colorless crystals; mp: 275-277° C.

EXAMPLE 9 trans-2,3-Bis(4-chlorophenyl)-N-(6-methylpyridin-2-yl)-1-oxo-1,2,3,4-tetrahydroisoquinoline-4-carboxamide (trans-7l): Quantities: trans-5f (1 mmol, 410 mg), NEt$_3$ (1 mmol, 140 µL), 2,2,2-trichloro-1,1-dimethylethyl chloroformiate (1.5 mmol, 360 mg) and 2-amino-6-picoline (1.5 mmol, 150 µL). The precipitate was filtered, dissolved in CHCl$_3$ and extracted with aqueous formic acid (5%). The organic layer was dried over Na$_2$SO$_4$ and evaporated. Crystallization from ethyl acetate gave trans-7l. Yield: 77%; colorless solid; mp: 241-242° C.

EXAMPLE 10 trans-2,3-Bis(3,5-dimethylphenyl)-N-(6-methylpyridin-2-yl)-1-oxo-1,2,3,4-tetrahydroisoquinoline-4-carboxamide (trans-7m): Quantities: trans-5g (1 mmol, 400 mg), NEt$_3$ (1 mmol, 140 µL), 2,2,2-trichloro-1,1-dimethylethyl chloroformiate (1.5 mmol, 360 mg) and 2-amino-6-picoline (1.5 mmol, 150 µL). The precipitate was filtered, dissolved in CHCl$_3$ and extracted with aqueous formic acid (5%). The organic layer was dried over Na$_2$SO$_4$ and evaporated. Crystallization from ethyl acetate gave trans-7m. Yield: 94%; colorless solid; mp: 281-283° C.

COMPARATIVE EXAMPLE 19 trans-3-(4-Methoxyphenyl)-N-(6-methylpyridin-2-yl)-1-oxo-2-(4-phenoxyphenyl)-1,2,3,4-tetrahydroisoquinoline-4-carboxamide (trans-7n): Quantities: trans-5h (1 mmol, 465 mg), NEt$_3$ (1 mmol, 140 µL), 2,2,2-trichloro-1,1-dimethylethyl chloroformiate (1.5 mmol, 360 mg) and 2-amino-6-picoline (1.5 mmol, 150 µL). The precipitate was filtered, dissolved in CHCl$_3$ and extracted with aqueous formic acid (5%). The organic layer was dried over Na$_2$SO$_4$ and evaporated. Crystallization from CHCl$_3$ gave trans-7n. Yield: 83%; colorless solid; mp: 240-242° C.

EXAMPLE 11 trans-2,3-Bis(4-hydroxyphenyl)-N-(6-methylpyridin-2-yl)-1-oxo-1,2,3,4-tetrahydroisoquinoline-4-carboxamide (trans-7o): Compound trans-7d (2 mmol, 1.0 g) was dissolved in abs. dichloromethane under Ar atmosphere and cooled to 0° C. Borone tribromide (24 mmol, 2.3 mL) was added dropwise to the stirred solution. After 2h the reaction was quenched with an excess of MeOH. The solvent evaporated and the residue was purified by column chromatography (silica gel 60, chloroform/ethanol 10:1) to give trans-7o. Yield: 61%; colorless solid; mp: 298-301° C. (decompn.).

EXAMPLE 12 trans-3-(4-Methoxyphenyl)-1-oxo-2-phenyl-N-(pyrimidin-2-yl)-1,2,3,4-tetrahydroisoquinoline-4-carboxamide (trans-7p): Quantities: trans-5b (0.7 mmol, 250 mg), N,N-diisopropylethylamine (0.7 mmol, 115 µL), 2,2,2-trichloro-1,1-dimethylethyl chloroformiate (1.0 mmol, 240 mg) and 2-aminopyrimidine (1.3 mmol, 130 mg). The solvent was reduced in vacuo and the residue was purified by column chromatography (silica gel 60, chloroform/ethanol 10:1) and crystallized from toluene to give trans-7p. Yield: 48%; colorless solid; mp: 273-275° C.

EXAMPLE 13 trans-3-(4-Methoxyphenyl)-1-oxo-2-phenyl-N-(pyridin-3-yl)-1,2,3,4-tetrahydroisoquinoline-4-carboxamide (trans-7q): Quantities: trans-5b (1.3 mmol, 500 mg), NEt$_3$ (1.3 mmol, 180 µL), 2,2,2-trichloro-1,1-dimethylethyl chloroformiate (2.0 mmol, 480 mg) and 3-aminopyridine (2.7 mmol, 250 mg). The solvent was reduced in vacuo and the residue was purified by column chromatography (silica gel 60, chloroform/ethanol 10:1) and crystallized from ethyl acetate to give trans-7q. Yield: 86%; colorless solid; mp: 219-221° C.

EXAMPLE 14 trans-N-(4,6-Dimethylpyridin-2-yl)-3-(4-methoxyphenyl)-1-oxo-2-phenyl-1,2,3,4-tetrahydroisoquinoline-4-carboxamide (trans-7r): Quantities: trans-5b (0.8 mmol, 300 mg), NEt$_3$ (0.8 mmol, 110 µL), 2,2,2-trichloro-1,1-dimethylethyl chloroformiate (1.2 mmol, 290 mg) and 2-amino-4,6-dimethylpyridine (1.6 mmol, 195 mg). The precipitate was filtered and crystallized from ethyl acetate to give trans-7r. Yield: 45%; colorless solid; mp: 265-267° C.

The invention claimed is:
1. A compound represented by the following formula (I) or a pharmaceutically acceptable salt thereof

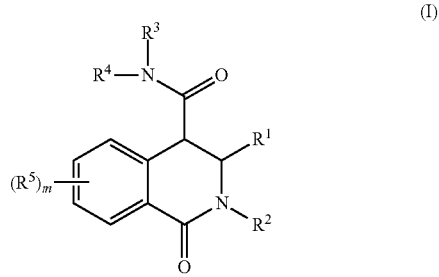

wherein
R$^1$ is phenyl, pyridinyl or pyrimidinyl, each of which may be substituted by one or more substituents Y;
R$^2$ is phenyl, pyridinyl or pyrimidinyl, each of which may be substituted by one or more substituents Y';

R³ is phenyl, pyridinyl or pyrimidinyl, each of which may be substituted by one or more substituents Y";

Y, Y' and Y" are independently selected from the group consisting of halogen, $C_{1-6}$ alkyl, $C_{1-6}$ haloalkyl, hydroxy, $C_{1-6}$ alkoxy, $C_{1-6}$ haloalkoxy, nitro, —NR⁶R⁷, —CO—R⁸, —CO—NR⁶R⁷, —COOR⁶, and —CO—NR⁶—CO—R⁸;

R⁴ is hydrogen or $C_{1-4}$ alkyl;

R⁵ is selected from the group consisting of halogen, hydroxy, $C_{1-6}$ alkyl, $C_{1-6}$ alkoxy, $C_{1-6}$ haloalkyl, $C_{1-6}$ haloalkoxy, nitro and —NR⁶R⁷;

R⁶ and R⁷ are independently selected from the group consisting of hydrogen and $C_{1-6}$ alkyl;

R⁸ is $C_{1-6}$ alkyl; and m is an integer ranging from 0 to 3, wherein if m is 2 or 3, the substituents R⁵ may be selected independently of each other;

provided that the compound of the formula (I) is not 2,3-bis(4-methoxyphenyl)-N-(6-methylpyridin-2-yl)-1-oxo-1,2,3,4-tetrahydroisoquinoline-4-carboxamide or 2,3-bis(4-methoxyphenyl)-1-oxo-N-(pyridin-2-yl)-1,2,3,4-tetrahydroquinoline-4-carboxamide.

2. The compound of claim 1, wherein R¹ and R² are phenyl.

3. The compound of claim 1, wherein R³ is phenyl or pyridinyl.

4. The compound of claim 1, wherein Y and Y' are independently selected from the group consisting of halogen, methyl, ethyl, methoxy and ethoxy.

5. The compound of any of claim 1, wherein Y" is methyl or ethyl.

6. The compound of claim 1, wherein R¹ and R², if substituted, bear at least one substituent at ortho or para position to the position at which R¹ and R² are attached to the tetrahydroisoquinolin-1-one ring.

7. The compound of claim 1, wherein R¹ and/or R² bear one substituent selected from halogen, methoxy and ethoxy at para position to the position at which R¹ and R² are attached to the tetrahydroisoquinolin-1-one ring.

8. The compound of claim 1, wherein R³ is pyridin-2-yl, 6-methylpyridin-2-yl, m-tolyl or 3,5-dimethylphenyl.

9. The compound of claim 1, wherein m is 0.

10. The compound of claim 1, wherein said compound takes the form of a trans enantiomer.

11. The compound of claim 1, selected from the group consisting of:
trans-N-(6-Methylpyridin-2-yl)-1-oxo-2,3-diphenyl-1,2,3,4-tetrahydroisoquinoline-4-carboxamide,
trans-3-(4-Methoxyphenyl)-N-(6-methylpyridin-2-yl)-1-oxo-2-phenyl-1,2,3,4-tetrahydroisoquinoline-4-carboxamide,
trans-2-(4-Methoxyphenyl)-N-(6-methylpyridin-2-yl)-1-oxo-3-phenyl-1,2,3,4-tetrahydroisoquinoline-4-carboxamide,
trans-2,3-Bis(4-methoxyphenyl)-1-oxo-N-(m-tolyl)-1,2,3,4-tetrahydroisoquinoline-4-carboxamide,
trans-N-(3,5-Dimethylphenyl)-2,3-bis(4-methoxyphenyl)-1-oxo-1,2,3,4-tetrahydroisoquinoline-4-carboxamide,
trans-2,3-Bis(4-fluorophenyl)-N-(6-methylpyridin-2-yl)-1-oxo-1,2,3,4-tetrahydroisoquinoline-4-carboxamide,
trans-2,3-Bis(4-chlorophenyl)-N-(6-methylpyridin-2-yl)-1-oxo-1,2,3,4-tetrahydroisoquinoline-4-carboxamide,
trans-3-(4-Methoxyphenyl)-1-oxo-2-phenyl-N-(pyrimidin-2-yl)-1,2,3,4-tetrahydroisoquinoline-4-carboxamide,
trans-3-(4-Methoxyphenyl)-1-oxo-2-phenyl-N-(pyridin-3-yl)-1,2,3,4-tetrahydroisoquinoline-4-carboxamide, and
trans-N-(4,6-Dimethylpyridin-2-yl)-3-(4-methoxyphenyl)-1-oxo-2-phenyl-1,2,3,4-tetrahydroisoquinoline-4-carboxamide.

12. A pharmaceutical composition comprising a compound of the formula (I) or a pharmaceutically acceptable salt thereof as defined in claim 1.

13. A method of treating a disease susceptible to the inhibition of the Heat Shock Protein 70(Hsp70), said method comprising the step of administering to a subject in need thereof an amount of a compound selected from the group consisting of the compound of formula (I) or a pharmaceutically acceptable salt thereof as defined in claim 1, 2,3-bis(4-methoxyphenyl)-N-(6-methylpyridin-2-yl)-1-oxo-1,2,3,4-tetrahydroisoquinoline-4-carboxamide and 2,3-bis(4-methoxyphenyl)-N-pyridin-2-yl-1-oxo-1,2,3,4-tetrahydroquinoline-4-carboxamide effective to inhibit the Hsp70 protein-mediated chaperone activity and induce caspase-dependent tumor-specific apoptosis, wherein said disease is multiple myeloma.

14. A method of treating a disease susceptible to the inhibition of the Heat Shock Protein 70 (Hsp70), said method comprising the step of administering to a subject in need thereof an amount of a compound selected from the group consisting of the compound of formula (I) or a pharmaceutically acceptable salt thereof as defined in claim 1, 2,3-bis(4-methoxyphenyl)-N-(6-methylpyridin-2-yl)-1-oxo-1,2,3,4-tetrahydroisoquinoline-4-carboxamide and 2,3-bis(4-methoxyphenyl)-N-pyridin-2-yl-1-oxo-1,2,3,4-tetrahydroquinoline-4-carboxamide effective to inhibit the Hsp70 protein-mediated chaperone activity and induce malignant growth and induce cell death, wherein said disease is cancer.

* * * * *

UNITED STATES PATENT AND TRADEMARK OFFICE
CERTIFICATE OF CORRECTION

Page 1 of 1

PATENT NO. : 9,975,853 B2
APPLICATION NO. : 15/316279
DATED : May 22, 2018
INVENTOR(S) : Manik Chatterjee et al.

It is certified that error appears in the above-identified patent and that said Letters Patent is hereby corrected as shown below:

On the Title Page

Under the heading "Applicant", at item (71), Lines 1-2, kindly delete the phrase "Julius-Maximilians-Universitaet Wuerzburg, Wuerzburg (DE)" and replace it with:
--Ulrike HOLZGRABE et al., Eibelstadt (DE)--.

After item (72), kindly insert new item (73) with the current Assignee information as follows:
--(73) Assignee: Ulrike HOLZGRABE et al., Eibelstadt (DE)--.

Signed and Sealed this
Sixteenth Day of April, 2019

Andrei Iancu
*Director of the United States Patent and Trademark Office*